United States Patent
Yun

(10) Patent No.: US 9,833,618 B2
(45) Date of Patent: Dec. 5, 2017

(54) METHODS AND COMPOSITIONS FOR TREATING A DISEASE CONDITION IN A SUBJECT

(75) Inventor: Anthony Joonkyoo Yun, Palo Alto, CA (US)

(73) Assignee: Palo Alto Investors, Palo Alto, CA (US)

( * ) Notice: Subject to any disclaimer, the term of this patent is extended or adjusted under 35 U.S.C. 154(b) by 2094 days.

(21) Appl. No.: 11/343,940

(22) Filed: Jan. 30, 2006

(65) Prior Publication Data

US 2006/0206149 A1 Sep. 14, 2006

Related U.S. Application Data

(60) Provisional application No. 60/649,933, filed on Feb. 4, 2005, provisional application No. 60/653,325, filed on Feb. 15, 2005, provisional application No. 60/692,534, filed on Jun. 20, 2005, provisional application No. 60/702,776, filed on Jul. 26, 2005.

(51) Int. Cl.
*A01N 43/00* (2006.01)
*A61K 31/33* (2006.01)
*A61N 1/32* (2006.01)
*A61N 2/00* (2006.01)

(52) U.S. Cl.
CPC ............ *A61N 1/326* (2013.01); *A61N 2/002* (2013.01)

(58) Field of Classification Search
USPC ........................................ 514/183
See application file for complete search history.

(56) References Cited

U.S. PATENT DOCUMENTS

| | | | | |
|---|---|---|---|---|
| 5,296,471 | A * | 3/1994 | Holme et al. | 514/56 |
| 5,741,283 | A * | 4/1998 | Fahy | 606/157 |
| 6,547,803 | B2 | 4/2003 | Seward et al. | |
| 2003/0055400 | A1 | 3/2003 | Seward et al. | |
| 2003/0171734 | A1* | 9/2003 | Seward et al. | 604/506 |
| 2003/0199852 | A1 | 10/2003 | Seward et al. | |
| 2003/0216758 | A1* | 11/2003 | Signore | 606/151 |
| 2004/0138643 | A1 | 7/2004 | Seward et al. | |
| 2004/0162542 | A1 | 8/2004 | Wilber et al. | |
| 2004/0204675 | A1 | 10/2004 | Seward et al. | |
| 2004/0213770 | A1 | 10/2004 | Seward et al. | |
| 2004/0223975 | A1 | 11/2004 | Brooks et al. | |

OTHER PUBLICATIONS

Huehns et al. Adventitia as a target for intravascular local drug delivery. Heart 75:537-538, 1996.*
Pliquett RU, Cornish KG, Zucker IH. Statin therapy restores sympathovagal balance in experimental heart failure. J Appl Physiol. 95(2):700-4, 2003.*
Ikeno et al (Catheterization and Cardiovascular Interventions 63:222-230, 2004).*
"Carotid Artery Disease", available online at: http://www.miamivascular.com/handler.cfm?event=practice,template&cpid=1528 (accessed Dec. 7, 2008).*
Ririe et al (Anesthesiology 109:698-706, 2008).*
Edelman et al (PNAS 87:3773-3777, 1990).*
Gotoh et al (Artioscler Thromb Vasc Biol 24:2063-2068, 2004).*
Gothoskar et al (Drug Delivery Technology, 4(5): Jun. 5, 2004).*
Caplan LR. Atherosclerotic Vertebral Artery Disease in the Neck. Curr Treat Options Cardiovasc Med. Jul. 2003;5(3):251-256.*
Hession WG, Stanczak JD, Davis KW, Choi JJ. Epidural steroid injections. Semin Roentgenol. Jan. 2004;39(1):7-23.*
Jukema JW, van der Hoorn JW. Amlodipine and atorvastatin in atherosclerosis: a review of the potential of combination therapy. Expert Opin Pharmacother. Feb. 2004;5(2):459-68.*
Stehbens WE. Mechanisms underlying arterial fragility and the complications of atherosclerosis. Pathobiology. 1997;65(1):1-13.*
Uhrich KE, Cannizzaro SM, Langer RS, Shakesheff KM. Polymeric systems for controlled drug release. Chem Rev. Nov. 10, 1999;99(11):3181-98.*

* cited by examiner

*Primary Examiner* — Marcos L Sznaidman
(74) *Attorney, Agent, or Firm* — Bret E. Field; Bozicevic, Field & Francis LLP

(57) ABSTRACT

Methods for treating a disease condition in a subject are provided. The subject methods include selectively modulating at least one biological activity of advential tissue in a manner effective to treat the disease condition. Also provided are compositions, kits and systems for use in practicing the subject methods.

20 Claims, 1 Drawing Sheet

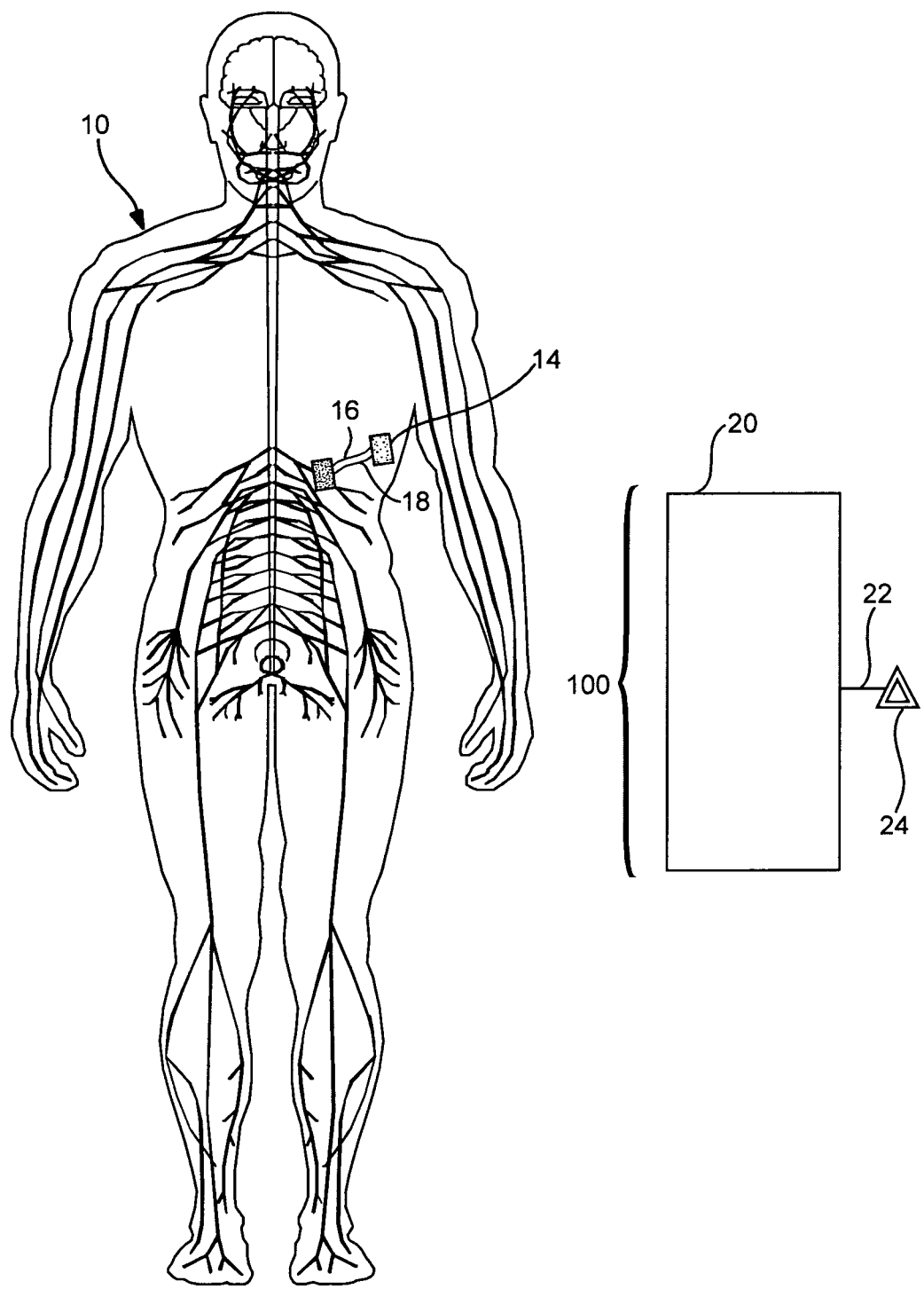

METHODS AND COMPOSITIONS FOR TREATING A DISEASE CONDITION IN A SUBJECT

CROSS-REFERENCE TO RELATED APPLICATIONS

Pursuant to 35 U.S.C. §119 (e), this application claims priority to the filing date of: U.S. Provisional Patent Application Ser. No. 60/649,933 filed on Feb. 4, 2005; U.S. Provisional Patent Application Ser. No. 60/653,325 filed on Feb. 15, 2005; U.S. Provisional Patent Application Ser. No. 60/692,534 filed on Jun. 20, 2005; and U.S. Provisional Patent Application No. 60/702,776 filed on Jul. 26, 2005; the disclosures of which applications are herein incorporated by reference.

INTRODUCTION

Background of the Invention

There are a variety of conditions that can affect an individual's health and well-being. The treatment of various conditions that affect the health and well-being of an individual has been around for centuries. In general, the armament of treatment options available to a physician to treat such conditions has increased tremendously, especially in the last century. However, while the number of treatment options has increased, typically such options are merely palliative, i.e., are designed for the relief of symptoms of a condition rather than actually being curative of the disorder itself. As such, there continues to be an interest in the development of new protocol options for treating conditions.

SUMMARY OF THE INVENTION

Methods for treating a disease condition in a subject are provided. The subject methods include selectively modulating at least one biological activity of adventitial tissue in a manner effective to treat the disease condition. Also provided are compositions, kits and systems for use in practicing the subject methods.

BRIEF DESCRIPTIONS OF THE DRAWINGS

FIG. 1 shows an exemplary embodiment of an electric energy applying device operatively positioned in a subject's body in accordance with embodiments of the subject methods.

DETAILED DESCRIPTION OF THE INVENTION

Methods for treating a disease condition in a subject are provided. The subject methods include selectively modulating at least one biological activity of adventitial tissue in a manner effective to treat the disease condition. Also provided are compositions, kits and systems for use in practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All patents, patent applications and publications mentioned herein are incorporated herein by reference to disclose and describe the methods and/or materials in connection with which the patents, patent applications and publications are cited. The citation of any patent, patent application and publication is for its disclosure prior to the filing date and should not be construed as an admission that the present invention is not entitled to antedate such patent, patent application and publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

Methods and Devices

Aspects of the invention include methods of treating a subject for a disease condition. In the subject methods, at least one biological activity of adventitial tissue is selectively modulated. In certain embodiments, the biological activity is an inflammatory activity, e.g., in the form of an inflammatory response. In certain embodiments, the biological activity is autonomic activity, e.g., in the form of the sympathetic/parasympathetic bias of the target adventitial tissue. In certain embodiments, the selective modulation is achieved by administering a pharmacological agent to the subject, e.g., in manner that selectively modulates target adventitial tissue. In certain embodiments, the selective modulation is achieved by applying electrical stimulation to the subject, e.g., in manner that selectively modulates target adventitial tissue. In certain embodiments, the disease condition is a vascular condition, such as a condition characterized by the presence of vascular occlusion and/or vascular inflammation. Also provided are algorithms, systems and kits that find use in practicing the subject methods.

Aspects of the present invention relate to pharmacologic, mechanical, and electrical systems for treating or preventing vascular inflammation, vascular occlusion, and/or other vascular diseases throughout the arteriovenous system, as well as any disease for which alteration in vascular biology, and specifically selectively alteration of adventitial biology, may alter prognosis or course. Specifically, the invention relates to drugs or devices that affect autonomic and inflammatory activity in the adventitia either through direct application to the surface of the adventitia, through specific targeting of the receptors in the adventitia, or through pharmacologic, mechanical, or electric modulation of baroreceptors, chemoreceptors, or volume sensors within or without the vessel wall. Embodiments of the invention specifically exclude introduction of genetic material into the adventitia.

It is an object and advantage of embodiments of the present invention to affect vessel biology through the specific modulation of adventitial biology. One aspect of the present invention involves the direct modulation of adventitial biology through delivery of agents to the adventitia. Any convenient protocol may be employed, including needle insertion into the vessel wall or external approaches involving application of polymer, reservoir, or adjunct vessel applied to the external aspect of the vessel. However, the invention is not so limited, such that any convenient mechanical and electrical approaches as well as more traditional pharmacologic avenues, may be employed.

Given the role of the adventitia as the destination for autonomic innervation of the vessel, another embodiment of the present invention comprises stimulation or inhibition of autonomic nerves that supply the target vessels under consideration via either pharmacologic action or via direct control of electrical activity, as in the case of electrode application.

Given the role of baroreceptors, chemoreceptors, and other sensors within the vessel wall as potential contributors to control of autonomic innervation of the vessel, another embodiment of the present invention comprises stimulation or inhibition of local receptors that influence the target vessels under consideration via either pharmacologic action or via direct control of electrical activity, as in the case of electrode application.

Given the rich vasculature of particular internal target organs, another embodiment of the present invention comprises partial or complete encapsulation of the internal target organ in order to generate a coordinated mechanical, electrical, or pharmacologic effect on the local vasculature throughout said structure, examples of which include, but are not limited to, the uterus.

Given the accessibility of the vasculature in particular anatomic locales, another embodiment of the present invention constitutes administration of the agent, be it mechanical, electrical, or pharmacologic, directly to an external or readily accessible internal anatomic site, examples of which include, but are not limited to, the female genitourinary tract.

Another embodiment of the present invention comprises systemic administration of pharmacologic agents with specific influence upon and activity within and unique to the adventitia.

Also disclosed is a method for monitoring the effects of treatment via sampling of pressure, volume, or oxygenation by proxy, with the additional aspect of ongoing dosage adjustment based on data thus acquired.

Embodiments of the invention include a method for treating or preventing vessel disease or derangement, or organ disease for which alteration of vessel biology could potentially influence the course or outcome of disease. The method involves administration of agents whose sole objective consists of altering the biology within the adventitia, the outer layer of the blood vessel wall. These agents may be administered or applied directly to the vessel, or may be administered or applied to remote sites with the intention of affecting the adventitia in a directed or specific manner. These agents may include, but are not limited to, small molecule or protein pharmacologic agents, direct or remote application of mechanical force, or direct or remote application of electrical energy. Pharmacologic agents may include, but are not limited to, anti-inflammatory, anti-infective, and neuromodulatory compounds. These agents may be administered constitutively or may be delivered in a pulsatile fashion, the schedule of which may be predetermined or in response to ongoing real-time or delayed measurements of desired target parameters.

In certain embodiments, the agents are pro parasympathetic agents. Representative pro parasympathetic agents of interest include, but are not limited to those listed in Table 1 below:

TABLE 1

| Drug Name |
|---|
| Beta Blockers |
| atenolol (Tenormin R) |
| betaxolol (Kerlone R) |
| bisoprolol (Zebeta R) |
| carvedilol (Coreg R) |
| esmolol (Brevibloc R) |
| labetalol (Normodyne R) |
| metoprolol (Lopressor R) |
| nadolol (Corgard R) |
| pindolol (Visken R) |
| propranolol (Inderal R) |
| sotalol (Betapace R) |
| timolol (Blocadren R) |
| Aldosterone Antagonists |
| Spironolactone |
| eplerenone |
| Angiotensin II Receptor Blockade |
| candesartan (Atacand R) |
| irbesartan (Avapro R) |
| losartan (Cozaar R) |
| telmisartin (Micardis R) valsartan (Diovan R) |
| eprosartan mesylate (Teveten) |
| ACE inhibitors |
| Benazepril (Lotensin R) |
| Captopril (Capoten R) |
| Enalapril (Vasotec R) |
| Fosinopril (Monopril R) |
| Lisinopril (Prinivil R) |
| Moexipril (Univasc R) |
| Quinapril (Accupril R) |
| Ramipril (Altace R) |
| Trandolapril (Mavik R) |
| Statins |
| atorvastatin (Lipitor R) |
| cerivastatin (Baycol R) |
| fluvastatin (Lescol R) |
| lovastatin (Mevacor R) |
| pravastatin (Pravachol R) |
| simvastatin (Zocor R) |
| Triglyceride Lowering Agents |
| fenofibrate (Tricor R) |
| gemfibrozil (Lopid R) |
| Niacin |

TABLE 1-continued

| Drug Name |
|---|
| Diabetes Agents |
| acarbose (Precose R) |
| glimepiride (Amaryl R) |
| glyburide (Micronase R, Diabeta R) |
| metformin (Glucophage R) |
| Miglitol (Glycet R) |
| pioglitazone (Actos R) |
| repaglinide (Prandin R) |
| rosiglitazone (Avandia R) |
| Immunomodulators |
| Interferon Alfa-2A (Roferon-A) |
| Interferon Alfa-2b (Intron-A) |
| Interferon Alfa-2b and Ribavirin combo Pack (Rebetron) |
| Interferon Alfa-N3 (Alferon N) |
| Interferon Beta-1A (Avonex) |
| Interferon Beta-1B (Betaseron) |
| Interferon Gamma |
| binds/reacts to CD4, gp39, B7, CD19, CD20, CD22, CD401, CD40, CD40L and CD23 antigens |
| rituximab |
| Nicotine |
| Sympathomimetics |
| trimethaphan |
| Clonidine |
| Reserpine |
| Guanethidine |
| Antihistamines |
| Benadryl |
| Diphenhydramine |
| Actifed (Triprolidine) PBZ (Tripelenamine) |
| Allegra (Fexofenadine) Periactin (Cyproheptadine) |
| Antivert or Bonine (Meclizine) Phenergan (Promethazine) |
| Astelin (dispensed as a Nose Spray) Polyhistine (Phenyltoloxamine) |
| Atarax (Hydroxyzine) Seldane (Terfenadine) |
| Benadryl (Diphenhydramine) Semprex (Acrivastine) |
| Bromfed (Brompheneramine) Tavist (Clemastine) |
| Chlortrimeton (Chlorpheniramine) Unisom (Doxylamine) |
| Claritin (Loratidine) Zyrtec (Cetirizine) |
| Dramamine (Dimenhydrinate) |
| Cholinergics |
| Bethanechol |
| Oxotremorine |
| Methacholine |
| Cevimeline |
| Carbachol |
| Galantamine |
| Arecoline |
| Levaminsole |
| Acetylcholinesteriase Inhibitors |
| Edrophonium |
| Neostigmine |
| Donepezil |
| Tacrine |
| Echothiophate |
| Diisopropylfluorophosphate |
| Demecarium |
| Pralidoxime |
| Galanthamine |
| Tetraethyl pyrophosphate |
| Parathoin |
| Malathion |
| Isoflurophate |
| Metrifonate |
| Physostigmine |
| Rivastigmine |
| Abenonium acetylchol |
| Carbaryl acetylchol |
| Propoxur acetylchol |
| Aldicarb acetylchol |

TABLE 1-continued

| Drug Name |
|---|
| Muscarinics |
| Muscarine |
| Pilocarpine |
| Magnesium**** |
| Calcium channel blockers**** |
| amlodipine besylate Norvasc |
| diltiazem hydrochloride Cardizem CD, Cardizem SR, Dilacor XR, Tiazac |
| felodipine Plendil |
| isradipine DynaCirc, DynaCirc CR |
| nicardipine Cardene SR |
| nifedipine Adalat CC, Procardia XL |
| nisoldipine Sular |
| verapamil hydrochloride Calan SR, Covera HS, Isoptin SR, Verelan |
| Sodium channel blockers**** |
| moricizine |
| propafenone |
| encainide |
| flecainide |
| Tocainide |
| mexiletine |
| Phenytoin |
| Lidocaine |
| Disopyramide |
| Quinidine |
| Procainamide |
| Glucocorticoid receptor blocker |
| (Mifepristone)**** |
| Peripheral adrenergic inhibitors |
| guanadrel Hylorel |
| guanethidine monosulfate Ismelin |
| reserpine Serpasil |
| Mecamylamine |
| Hexemethonium |
| Blood vessel dilators |
| hydralazine hydrocholoride Apresoline |
| minoxidil Loniten** |
| Central agonists |
| alpha methyldopa Aldomet |
| clonidine hydrochloride Catapres |
| guanabenz acetate Wytensin |
| guanfacine hydrochloride Tenex |
| Combined alpha and beta blockers |
| labetolol hydrochloride, Normodyne, Trandate |
| carvedilol Coreg |
| Alpha blockers |
| doxazosin mesylate Cardura |
| prazosin hydrochloride Minipress |
| terazosin hydrochloride Hytrin |
| Combination diuretics |
| amiloride hydrochloride + hydrochlorothiazide Moduretic |
| spironolactone + hydrochlorothiazide Aldactazide |
| triamterene + hydrochlorothiazide Dyazide, Maxzide |
| Potassium-sparing diuretics |
| amiloride hydrochloride Midamar |
| spironolactone Aldactone |
| triamterene Dyrenium |
| Nitrate pathway modulation agents |
| L-arginine |
| Nitroglycerin Deponit |
| Minitran |
| Nitropar |
| Nitrocine |
| Nitro Disc |
| Nitro-Dur |

TABLE 1-continued

| Drug Name |
|---|
| Nitrogard |
| Nitroglycerin |
| Nitroglycerin T/R |
| Nitro-Time |
| Nitrol ointment, Nitrolingual Spray |
| Nitrong, |
| Nitro-Bid, |
| Nitropress, |
| Nitroprex, |
| Nitro S.A., |
| Nitrospan, |
| Nitrostat, |
| Nitro-Trans System, |
| Nitro-Transdermal, |
| Nitro-Time, |
| Transderm-Nitro, |
| Tridil. Pentaerythrito I Tetranitrate |
| Peritrate, |
| Peritrate S.A |
| Erythrityl Tetranitrate |
| Cardilate |
| Isosorbide Dinitrate/Phenobarbital Isordil w/PB Isosorbide Mononitrate |
| Imdur |
| , ISMO, |
| Isosorbide Mononitrate, |
| Monoket |
| Isosorbide Nitrate |
| Cyclic nucleotide monophosphodiesterase (PDE) inhibitor |
| Levitra (vardenafil), |
| Cialis (tadalafil) |
| Viagra (sildenafil) |
| Vasopressin inhibitors |
| atosiban |
| Alcohol |
| Relaxin |
| Renin inhibitors |
| Aliskiren |
| Estrogen and estrogen analogues and estrogen metabolites |
| Vesicular monoamine transport (VMAT) inhibitors |
| reserpine |
| tetrabenazine |
| Melatonin |
| Melatonin Analogues |
| 6-chloromelatonin |
| 2,3-dihydromelatonin |
| 6-chloro-2,3-dihydromelatonin |
| N-acetyl-N2-formyl-5-methoxy kynurenamine |
| N-acetyl-5-methoxy kynurenamine |
| Progesterone inhibitors |
| ru486 |
| Testosterone inhibitors |
| Spironolactone |
| cyproterone acetate |
| Gonadotropin-releasing hormone inhibitors |
| Leuprolide Acetate |
| Oxytocin inhibitors |
| Terbutaline |
| Ritodrine |
| Glucagon Like Peptide 1 |
| Dipeptidyl Peptidase IV inhibitors |
| LAF237 (novartis) |
| P93/01 and P32/98 (Probiodrug AB) |

TABLE 1-continued

| Drug Name |
|---|
| valine pyrrolidide (Novo Nordisk) |
| dhea |
| adiponectin |
| phenserine |
| phosphodiesterase 4 inhibitor |
| valproate |
| Anticoagulants |
| Exanta (ximelagatran)- |
| Bilivarudin (hirulog) |
| abciximab (Reopro ®): |
| Aggrenox ® (dipridamole/ASA): |
| anagrelide (Agrylin ®): |
| clopidogrel (Plavix) |
| dipyridamole (Persantine ®): |
| tifabatide (Integrelin) |
| ticlopidine (Ticlid ®): |
| tirofiban (aggrastat) |
| ardeparin (Normiflo) |
| Dalteparin (Fragmin) |
| Danaparoid (Orgaran) |
| Enoxaparin (lovenox) |
| lepirudin (Refludan) |
| Heparin |
| Warfarin |
| Thrombolytics |
| alteplase (Activase ®, t-PA): |
| reteplase (Retevase) |
| Streptokinase |
| Urokinase |
| Other anticoagulants |
| aminocaproic acid (Amicar ®): |
| cilostazol (Pletal) |
| erythropoietin (Epogen) |
| filgrastim (G-CSF, Neupogen ®): |
| oprelvekin (Neumega) |
| pentoxifylline (Trental) |
| hmg1 antagonists |
| Neurotxins |
| capsaicin |
| resinoferatoxin |
| α-bungotoxin, |
| terodotoxin |
| botulinum toxin (botox) |

Advantages of embodiments of the invention include the ability to avoid direct disturbance of extant derangement within the vessel lumen or the inner layers of the vessel. Although the adventitia may serve as the site of regulation of the processes that lead to such pathology, direct interaction with such elements may potentially lead to activation of other pathways that could potentially amplify or escalate the extant pathology via feed-forward mechanisms.

Another embodiment comprises a method for altering adventitial biology through modulation of autonomic innervation. Modulation may occur through direct electrical stimulation or inhibition of relevant autonomic nerves either within the adventitia, proximal to the target vessel, or at a remote site. Modulation may occur through direct administration of neuromodulatory agents either within the adventitia, proximal to the target vessel, or at a remote site. Modulation may occur through feedback stimulation or inhibition of autonomic innervation via direct mechanical force imposed within the adventitia, on the surface of the target vessel, or at a remote site. Once again, these agents may be administered constitutively or may be delivered in a pulsatile fashion, the schedule of which may be predetermined or may occur in response to ongoing real-time or delayed measurements of desired target parameters.

Another embodiment comprises a method for altering adventitial biology through modulation of autonomic innervation by influencing upstream control elements such as baroreceptors, chemoreceptors, and other volume sensors. Modulation may occur through direct electrical stimulation or inhibition of relevant sensor structures within the target vessel, proximal to the target vessel, or at a remote site. Modulation may occur through direct administration of agents to modify parameters measured by these sensors or by administration of neuromodulatory agents to alter the nature of either the afferent or efferent signals received or produced by these sensors. Once again, these agents may be administered constitutively or may be delivered in a pulsatile fashion, the schedule of which may be predetermined or may occur in response to ongoing real-time or delayed measurements of desired target parameters.

Another embodiment comprises a method for altering adventitial biology through complete or partial encapsulation of the organ upon or in which the target vessels reside. Encapsulation may occur through direct application of a biopolymer to the surface of the organ or may occur through application of an external structure constructed of biocompatible materials otherwise lacking intrinsic biologic activity. Candidate materials used in other applications would include stainless steel, Elgiloy, titanium, tantalum, Nitinol, ePTFE, collagen, nylon, polyester, and urethane. Relevant agents for delivery could be applied to the surface of such a structure prior to apposition, or the structure apposed to the target organ in its native form, to exert influence purely via its mechanoresistive properties.

A great advantage of the aforementioned embodiment is the ability to administer interventions in a coordinated, synchronized fashion for the whole of a series or systems for which the approach may hold relevance. It also enables the consideration of regional application as opposed to purely local or systemic administration of agents in order to further define an intermediate sphere of control which may have specific advantages for influencing processes that operate within the confines of a particular organ, a oligarchic yet still heterogenous assemblage of elements, rather than in a particular type of structure, i.e. the blood vessel, or throughout the entire body.

Another aspect of this embodiment comprises the application of active power to the structure in order to alter resistive force and thus create bending moments that exert controlled degrees of compression, again either administered constitutively or delivered in a pulsatile fashion, the schedule of which may be predetermined or may occur in response to ongoing real-time or delayed measurements of desired target parameters.

Another embodiment comprises a method for altering adventitial biology through application of an agent to a remote locale that contains vessels harboring adventitia but that otherwise bears no specific functional connection to the target in question or for which any local activity realized departs from the ultimate objective for administration, but that offers ready access for administration and which can subsequently serve as the portal for transport or conductance to the ultimate site of action. Such an embodiment would include methods for delivery and administration via direct application to the oropharyngeal cavity and the genitourinary tract. Agents that would operate in this capacity would include electrical via local nerve conductance, pharmacologic via transduction by electrical/chemical proxy, and mechanical via physical transduction of force.

Another embodiment comprises a method for altering adventitial biology through systemic administration of a pharmacologic agent specifically targeted to the adventitia or to affect processes in the adventitia through a remote target.

An aspect of each of these aforementioned embodiments involves either real-time or delayed modulation of administration of agents and interventions by sampling specific parameters that would indicate potential efficacy and propriety of action. Such parameters may include, but are not limited to, blood oxygenation, pH, pressure, and volume. Measurements may be conducted locally, regionally, or systemically via relevant optical and electromechanical techniques. Data acquired in said fashion would then bemused to adjust the schedule and dosage of administration appropriately in order to achieve desired objectives.

As such, features of the subject invention include methods for treatment or prevention of vessel or organ disease for which alteration of vessel biology influences the progression or outcome of disease, where treatment includes the specific modulation of adventitial biology. A representative sampling of such diseases would include, but not necessarily be limited to, aortic aneurysms, renal disease, stenosis of any vessel, vasculitis, diabetes mellitus, and stroke. In certain embodiments, pharmacologically active small molecules are employed. In certain embodiments, the methods modulate immunologic activity. In certain embodiments, the methods modulate autonomic activity. In certain embodiments, the methods modulate infectious activity. In certain embodiments, the methods employ a pharmacologically active protein. In certain embodiments, the methods include application of electrical current. In certain embodiments, the methods include application of physical force. In certain embodiments, the methods include direct application of a stimulus to the adventitia of the target vessel/s. In certain embodiments, the methods include direct application of a stimulus to the adventitia of vessels adjoining the target vessel/s. In certain embodiments, the methods include direct application of a stimulus to the autonomic nerves supplying the adventitia of the target vessel/s. In certain embodiments, the methods include direct application of a stimulus to the baroreceptors influencing the biology of the adventitia of the target vessel/s. In certain embodiments, the methods include direct application of a stimulus to the chemoreceptors influencing the biology of the adventitia of the target vessel/s. In certain embodiments, the methods include direct application of a stimulus to the volume receptors influencing the biology of the adventitia of the target vessel/s. In certain embodiments, the methods include direct application of a stimulus to adjacent readily accessible tissue structures physically linked to the adventitia of the target vessel/s. In certain embodiments, the methods include systemic administration of a pharmacologically active small molecule linked to carrier molecule targeted to specific receptors in the adventitia. Also provided are methods wherein a device measuring the desired outcome of the method modulates the subsequent instruction for the method in conjunction with or independent of additional operator intervention. In certain embodiments, the parameter measured is blood oxygenation. In certain embodiments, the parameter measured is blood acidity (pH). In certain embodiments, the parameter measured is intraluminal pressure. In certain embodiments, the parameter measured is intraluminal volume.

Administering a Pharmacological Agent

In certain embodiments, the subject invention includes administering an effective amount of a pharmacological agent to a subject. Any suitable pharmacological agents may be administered. That is, embodiments of the subject methods include administering an effective amount, i.e., a therapeutically effective amount, of one or more pharmacological agents to a subject. By "effective amount" is meant a dosage sufficient to cause the subject to mount a compensatory response effective to treat the subject, as desired. The effective amount will vary with the age and physical condition of the subject, severity of the condition being treated, the duration of the treatment, the nature of any concurrent treatment, the pharmaceutically acceptable carrier used if any, and analogous factors within the knowledge and expertise of those skilled in the art.

In certain embodiments, more than one type of agent may be administered at the same or different times to treat the same or different condition. The effective amount of a given agent may vary somewhat from subject to subject, and may depend upon factors such as, but not limited to, the age and condition of the subject, the form of the agent, the route and method of delivery, etc., as noted above. Dosages may be determined in accordance with routine pharmacological procedures known to those skilled in the art.

Depending on the particular agent(s) administered to a subject, the agent(s) may be administered to a subject using any convenient means. Thus, a pharmacological agent may be incorporated into a variety of formulations for administration to a subject. A pharmacological agent may be formulated into pharmaceutical compositions by combination with appropriate, pharmaceutically acceptable carriers. By "pharmaceutically acceptable carrier" is meant a component such as a carrier, diluent, excipient, and the like of a composition that is compatible with the one or more pharmacological agents and other optional ingredients of the subject pharmacological agent compositions in that a pharmaceutically acceptable carrier may be combined with the pharmacological agent(s) without eliminating the biological or therapeutically effective activity of the one or more pharmacological agents, and is suitable for use in subjects as provided herein without undue adverse side effects (such as toxicity, irritation, allergic response, and death). Side effects are "undue" when their risk outweighs the benefit provided by the pharmaceutical agent. Non-limiting examples of pharmaceutically acceptable components include, but are not limited to, any of the standard pharmaceutical carriers such as phosphate buffered saline solutions, water, emulsions such as oil/water emulsions or water/oil emulsions, microemulsions, and various types of wetting agents. Accordingly, the pharmacological agents employed in the subject methods may be formulated into preparations in solid, semi-solid (e.g., gel), liquid or gaseous forms, such as tablets, capsules, powders, granules, ointments, solutions, suppositories, injections, inhalants and aerosols. As such, administration of a pharmacological agent may be achieved in various ways, including, but not limited to, oral, buccal (e.g. sub-lingual), rectal, topical (including both skin and mucosal surfaces, including airway surfaces), parenteral (e.g., subcutaneous, intramuscular, intradermal, intravenous and intrathecal), intraperiactivityal, transdermal, intracheal, intravaginal, endocervical, intrathecal, intranasal, intravesicular, in or on the eye, in the ear canal, etc., administration. In certain embodiments, one or more pharmacological agents may be administered via a transdermal patch or film system such as or analogous to that described, e.g., in U.S. Pat. Nos. 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; and 4,585,452, the disclosures of which are herein incorporated by reference.

Embodiments may include pharmacological agent formulations for oral administration that may be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use may be obtained through combination of at least one pharmacological agent with a solid excipient, optionally grinding a resulting mixture, and processing the mixture of granules, after adding suitable additional compounds, if desired, to obtain tablets or dragee cores. Suitable solid excipients include, but are not limited to, carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate; with optional lubricants, such as talc or magnesium stearate; and if desired, with diluents, buffering agents, moistening agents, preservatives and flavoring agents.

Accordingly, pharmacological agent formulations suitable for oral administration in accordance with the subject invention may be present in discrete units, such as capsules, cachets, lozenges, tablets, and the like, each containing a predetermined amount of the active pharmacological agent; as a powder or granules; as a solution or a suspension in an aqueous or non-aqueous liquid; or as an oil-in-water or water-in-oil emulsion. Such pharmacological agent formulations may be prepared by any suitable method of pharmacy which includes, but is not limited to, bringing into association the active pharmacological agent and a suitable carrier (which may contain one or more optional ingredients as noted above). For example, pharmacological agent formulations for use with the subject invention may be prepared by uniformly and intimately admixing the active pharmacological agent(s) with a liquid or finely divided solid carrier, or both, and then, if necessary, shaping the resulting mixture. For example, a tablet may be prepared by compressing or molding a powder or granules containing the active pharmacological agent, optionally with one or more accessory ingredients. Compressed tablets may be prepared by compressing, in a suitable machine, the pharmacological agent in a free-flowing form, such as a powder or granules optionally mixed with a binder, lubricant, inert diluent, and/or surface active/dispersing agent(s). Molded tablets may be made by molding, in a suitable machine, the powdered pharmacological agent moistened with an inert liquid binder.

Pharmacological agents may also be administered in the form of suppositories for rectal administration of the drug. These formulations may be prepared by mixing a pharmacological agent with a suitable non-irritating vehicle or excipient which is solid at ordinary temperatures but liquid at the rectal temperatures and will therefore melt in the rectum to release the drug. Such materials include, but are not limited to, cocoa butter, carbowaxes and polyethylene glycols. Embodiments include one or more pharmacological agent(s) made into suppositories by mixing with a variety of bases such as emulsifying bases or water-soluble bases. Pharmacological agents may also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

For example, embodiments may also include at least one pharmacological agent in an aerosolized, atomized or nebulized vapor form, e.g., administrable via a metered dose device or nebulizer, and the like such that embodiments also include aerosolizing, vaporing or nebulizing one or more pharmacological agents for administration to a subject. Accordingly, the one or more pharmacological agent agents may be utilized in aerosol formulation or an analogous formulation to be administered via inhalation or analogous means. The one or more pharmacological agents employed in the practice of the present invention may be formulated into pressurized acceptable propellants such as dichlorodifluoromethane, propane, nitrogen and the like.

Pharmacological agents may be delivered transdermally, by a topical route, formulated as applicator sticks, solutions, suspensions, emulsions, gels, creams, ointments, pastes, jellies, paints, powders, and aerosols. For example, embodiments may include a pharmacological agent formulation in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agent(s) are retained. The base or matrix layer may be operatively associated with a support or backing. Pharmacological agent formulations suitable for transdermal administration may also be delivered by iontophoresis and may take the form of an optionally buffered aqueous solution of the pharmacological agent compound. Suitable formulations may include citrate or bis/tris buffer (pH 6) or ethanol/water and contain a suitable amount of active ingredient.

Pharmacological agents may be delivered as microspheres for slow release in the body. For example, microspheres may be administered via intradermal injection of drug-containing microspheres, which slowly release subcutaneously (see Rao, *J. Biomater Sci. Polym. Ed.* 7:623-645, 1995); as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

Pharmacological agents may be provided as a salt and may be formed with one or more acids, including but not limited to hydrochloric, sulfuric, acetic, lactic, tartaric, malic, succinic, etc. Salts tend to be more soluble in aqueous or other protonic solvents that are the corresponding free base forms. In other cases, a preparation may be a lyophilized powder that is combined with buffer prior to use. Pharmacological agents may be administered parenterally, such as intravenous (IV) administration, and may include a solution of the pharmacological agent dissolved in a pharmaceutically acceptable carrier. Among the acceptable vehicles and solvents that may be employed, include, but are not limited to, water and Ringer's solution, an isotonic sodium chloride, etc. In addition, sterile fixed oils may conventionally be employed as a solvent or suspending medium. For this purpose any bland fixed oil may be employed including synthetic mono- or diglycerides. In addition, fatty acids such as oleic acid can likewise be used in the preparation of injectables. Accordingly, a pharmacological agent may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of pharmacological agent in these formulations may vary widely, and will be selected based on fluid volumes, viscosities, body weight, and the like, in accordance with the particular mode of administration selected and the patient's needs. For IV administration, the formulation may be a sterile injectable preparation, such as a sterile injectable aqueous or oleaginous suspension. This suspension may be formulated according to the known art using those suitable dispersing or wetting agents and suspending agents. The sterile injectable preparation may also be a sterile injectable solution or suspension in a nontoxic parenterally-acceptable diluent or solvent, such as a solution of 1,3-butanediol, and the like. Accordingly, pharmacological agent formulations suitable for parenteral administration may include sterile aqueous and non-aqueous injection solutions of one or more active pharmacological agent agents, which preparations may be isotonic with the blood of the intended recipient. These preparations may contain buffers and solutes which render the formulation isotonic with the blood of the intended recipient. Aqueous and non-aqueous sterile suspensions may include suspending agents and thickening agents. The formulations may be presented in single- or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind described above.

Pharmacological agents may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the pharmacological agent into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). Accordingly, embodiments may include one or more pharmacological agents administered as liposomal formulations of the pharmacological agents. Methods for preparing liposomal suspensions are known in the art and thus will not be described herein in great detail. Briefly, in those embodiments where the pharmacological agent is an aqueous-soluble pharmacological agent, the pharmacological agent may be incorporated into lipid vesicles using conventional liposome technology. In such instances, due to the water solubility of the pharmacological agent, the pharmacological agent may be substantially entrained within the hydrophilic center or core of the liposomes. The lipid layer employed may be of any conventional composition and may either contain cholesterol or may be cholesterol-free. When the pharmacological agent of interest is water-insoluble, the pharmacological agent may be substantially entrained within the hydrophobic lipid bilayer which forms the structure of the liposome employing conventional liposome formation technology. In either instance, the liposomes that may be produced may be reduced in size, as through the use of standard sonication and homogenization techniques. Embodiments of liposomal formulations containing the pharmacological agent of interest may be lyophilized to produce a lyophilizate which may be reconstituted with a pharmaceutically acceptable carrier, such as water, to regenerate a liposomal suspension.

A pharmaceutical composition of the subject invention may optionally contain, in addition to a pharmacological agent, at least one other therapeutic agent useful in the treatment of a condition. Such other compounds may be of any class of drug or pharmaceutical agent, including but not limited to antibiotics, anti-parasitic agents, antifungal agents, anti-viral agents, anti-tumor agents, anti-neurodegenerative agents and anti-psychotic agents. When administered with anti-parasitic, anti-bacterial, antifungal, anti-tumor, anti-viral agents, anti-neurodegenerative, and anti-psychotic agents and the like, pharmacological agents may be administered by any method and route of administration suitable to the treatment of the condition, typically as pharmaceutical compositions.

Pharmacological agents may include pharmacological agent compositions that may be prepared from water-insoluble compounds, or salts thereof, such as aqueous base emulsions. In such embodiments, the pharmacological agent composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

As noted above, in addition to active pharmacological agent agents, the pharmaceutical pharmacological agent compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Furthermore, pharmacological agent compositions may, though not always, contain microbial preservatives. Microbial preservatives that may be employed include, but are not limited to, methylparaben, propylparaben, and benzyl alcohol. The microbial preservative may be employed when the pharmacological agent formulation is placed in a vial designed for multidose use. Pharmaceutical pharmacological agent compositions for use in practicing the subject methods may be lyophilized using techniques well known in the art.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Embodiments may also include administration of at least one pharmacological agent using a pharmacological delivery device such as, but not limited to, pumps (implantable or external devices), epidural injectors, syringes or other injection apparatus, catheter and/or reservoir operatively associated with a catheter, etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert the at least one pharmacological agent into the delivery device for administration of the pharmacological agent to a subject and include, but are not limited to, vials, ampules, tubes, capsules, bottles, syringes and bags.

In certain embodiments, a pharmaceutically acceptable carrier may be preservative free. By "preservative free" is meant the substantial absence of chemical, antibacterial, antimicrobial, or antioxidative additives, or the like, from the pharmaceutically acceptable carriers of the present invention. "Substantial absence" may mean that no preservative is present in the compositions or that trace amounts may be present that impart no detectable effect otherwise attributable to a preservative. For example, the pharmaceutically acceptable carrier may be characterized by the substantial absence of chemical, antibacterial, antimicrobial, or antioxidative additives or the like (e.g., contain less than about 5.0, 4.0, 3.0, 2.0, 1.0, 0.5, 0.1, 0.05, 0.01, or even about 0.00 percent by weight of a preservative). Further, such formulations may be substantially or essentially free of alcohols such as ethanol (e.g., contain less than about 5.0, 4.0, 3.0, 2.0, 1.0, 0.5, 0.1, 0.05, 0.01, or even about 0.00 percent by weight of alcohols such as ethanol). Examples of suitable pharmacological agent formulations include, but are not limited to, formulations that include one or more active pharmacological agent agents and physiological saline solution (optionally including other typical ingredients such as other active agents and buffers).

As noted above, in pharmaceutical dosage forms, agents may be administered alone or with or in appropriate association, as well as in combination, with other pharmaceutically active compounds. As used herein, "administered with" means that at least one pharmacological agent and at least one other adjuvant (including one or more other pharmacological agents) are administered at times sufficiently close that the results observed are indistinguishable from those achieved when one pharmacological agent and at least one other adjuvant (including one or more other pharmacological agents) are administered at the same point in time. The pharmacological agent and at least one other adjuvant may be administered simultaneously (i.e., concurrently) or sequentially. Simultaneous administration may be carried out by mixing the at least one pharmacological agent and at least one other adjuvant prior to administration, or by administering the pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that the at least one pharmacological agent and at least one other adjuvant are administered at the same point in time or immediately following one another. In the latter case, the at least one pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Unit dosage forms for oral or rectal administration such as syrups, elixirs, and suspensions may be provided wherein each dosage unit, for example, teaspoonful, tablespoonful, tablet or suppository, contains a predetermined amount of a pharmacological agent. Similarly, unit dosage forms for injection or intravenous or other suitable administration route may include the pharmacological agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of pharmacological agent calculated in an amount sufficient to produce the desired effect in association with a pharmaceutically acceptable diluent, carrier or vehicle. The specifications for the unit dosage forms of pharmacological agents of the present invention depend on, for example, the particular pharmacological agent(s) employed and the effect to be achieved, the pharmacodynamics associated with the particular pharmacological agent(s) in the subject, etc.

Embodiments include administering an effective amount of a first agent and an effective amount of a second agent. For example, embodiments may include administering a first agent and a second agent to provide an enhanced therapeutic effect. By "enhanced therapeutic effect" is meant that at least the desired outcome occurs more quickly and/or is of greater magnitude with a combination of the pharmacological agents, as compared to the same doses of each component given alone; or that doses of one or all component(s) are below what would otherwise be a minimum effective dose (a "sub-MED").

Any two pharmacological agents may be given in close enough temporal proximity to allow their individual therapeutic effects to overlap. For example, embodiments of the subject invention include the co-timely administration of a first and second agent, where "co-timely" is meant administration of a second pharmacological agent while a first pharmacological agent is still present in a subject in a therapeutically effective amount. It is to be understood that in some instances this will require sequential administration. Alternatively, multiple routes of administration may be employed, e.g., intravenous or subcutaneous injection combined with oral administration, and the like.

Embodiments also include pharmaceutical compositions in unit dosage forms that are useful which contain more than one type of pharmacological agent. In other words, a single agent administration entity may include two or more pharmacological agents. For example, a single tablet, capsule, dragee, trocheem suppository, syringe, and the like, combining two or more pharmacological agents would be a unit dosage form. The therapeutic agents present in a unit dosage form may be present in amounts such that, upon administration of one or more unit doses of the composition, a subject experiences, e.g., a longer lasting efficacy than with the administration of either agent alone and/or greater magnitude and/or quicker lowering of action. Such compositions may be included as part of a therapeutic package in which one or more unit doses are placed in a finished pharmaceutical container. Labeling may be included to provide directions for using the composition according to the invention. The actual amounts of each agent in such single unit dosage forms may vary according to the specific compositions being utilized, the particular compositions formulated, the mode of application, the particular route of administration, and the like, where dosages for a given subject may be determined using conventional considerations, e.g., by customary comparison of the differential activities of the subject compositions and of a known agent, or by means of an appropriate, conventional pharmacological protocol.

In certain embodiments, the pharmacological agent(s) is present in (and therefore administered in) a controlled release formulation. Controlled release formulations within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, Extended-Release Dosage Forms, 1987 (CRC Press, Inc.).

There are companies with specific expertise in drug delivery technologies including controlled release oral formulations such as Alza Corporation and Elan Pharmaceuticals, Inc. A search of patents, published patent applications and related publications will provide those skilled in the art reading this disclosure with significant possible controlled release oral formulations. Examples include the formulations disclosed in any of the U.S. Pat. No. 5,637,320 issued Jun. 10, 1997; U.S. Pat. No. 5,505,962 issued Apr. 9, 1996; U.S. Pat. No. 5,641,745 issued Jun. 24, 1997; and U.S. Pat. No. 5,641,515 issued Jun. 24, 1997. Although specific formulations are disclosed here and in these patents, the invention is more general than any specific formulation.

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, Controlled Release Technologies: Methods, Theory and Applications, 1980 (CRC Press, Inc.).

Controlled release drug delivery systems may also be categorized under their basic technology areas, including, but not limited to, rate-preprogrammed drug delivery systems, activation-modulated drug delivery systems, feedback-regulated drug delivery systems, and site-targeting drug delivery systems.

In rate-preprogrammed drug delivery systems, release of drug molecules from the delivery systems "preprogrammed" at specific rate profiles. This may be accomplished by system design, which controls the molecular diffusion of drug molecules in and/or across the barrier medium within or surrounding the delivery system. Fick's laws of diffusion are often followed.

In activation-modulated drug delivery systems, release of drug molecules from the delivery systems is activated by some physical, chemical or biochemical processes and/or facilitated by the energy supplied externally. The rate of drug release is then controlled by regulating the process applied, or energy input.

In feedback-regulated drug delivery systems, release of drug molecules from the delivery systems may be activated by a triggering event, such as a biochemical substance, in the body. The rate of drug release is then controlled by the concentration of a triggering agent detected by a sensor in the feedback regulated mechanism.

In a site-targeting controlled-release drug delivery system, the drug delivery system targets the active molecule to a specific site or target tissue or cell, e.g., adventitial tissue. This may be accomplished, for example, by a conjugate including a site specific targeting moiety that leads the drug delivery system to the vicinity of a target tissue (or cell), a solubilizer that enables the drug delivery system to be transported to and preferentially taken up by a target tissue, and a drug moiety that is covalently bonded to the polymer backbone through a spacer and contains a cleavable group that can be cleaved only by a specific enzyme at the target tissue.

While a preferable mode of controlled release drug delivery will be oral, other modes of delivery of controlled release compositions according to this invention may be used. These include mucosal delivery, nasal delivery, ocular delivery, transdermal delivery, parenteral controlled release delivery, vaginal delivery, and intrauterine delivery.

There are a number of controlled release drug formulations that are developed preferably for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems maybe found in Yie W. Chien, Novel Drug Delivery Systems, 1992 (Marcel Dekker, Inc.). Some of these formulations will now be discussed in more detail.

Enteric coatings are applied to tablets to prevent the release of drugs in the stomach either to reduce the risk of unpleasant side effects or to maintain the stability of the drug which might otherwise be subject to degradation due to exposure to the gastric environment. Most polymers that are used for this purpose are polyacids that function by virtue or the fact that their solubility in aqueous medium is pH-dependent, and they require conditions with a pH higher then that which is normally encountered in the stomach.

One type of oral controlled release structure is enteric coating of a solid or liquid dosage form. Enteric coatings promote the active agent's remaining physically incorporated in the dosage form for a specified period when exposed to gastric juice. Yet the enteric coatings are designed to disintegrate in intestinal fluid for ready absorption. Delay of the active agent's absorption is dependent on the rate of transfer through the gastrointestinal tract, and so the rate of gastric emptying is an important factor. Some investigators have reported that a multiple-unit type dosage form, such as granules, may be superior to a single-unit type. Therefore, in a preferable embodiment, the active agent's may be contained in an enterically coated multiple-unit dosage form. In a more preferable embodiment, the dosage form is prepared by spray-coating granules of a active agent-enteric coating agent solid dispersion on an inert core material. These granules can result in prolonged absorption of the drug with good bioavailability.

Typical enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa, Application of solid dispersions of Nifedipine with enteric coating agent to prepare a sustained-release dosage form, Chem. Pharm. Bull. 33: 1615-1619 (1985). Various enteric coating materials may be selected on the basis of testing to achieve an enteric coated dosage form designed ab initio to have a preferable combination of dissolution time, coating thicknesses and diametral crushing strength. S. C. Porter et al., The Properties of Enteric Tablet Coatings Made From Polyvinyl Acetate-phthalate and Cellulose acetate Phthalate, J. Pharm. Pharmacol. 22:42p (1970).

On occasion, the performance of an enteric coating may hinge on its permeability. S. C. Porter et al., The Permeability of Enteric Coatings and the Dissolution Rates of Coated Tablets, J. Pharm. Pharmacol. 34: 5-8 (1981). With such oral drug delivery systems, the drug release process may be initiated by diffusion of aqueous fluids across the enteric coating. Investigations have suggested osmotic driven/rupturing affects as important release mechanisms from enteric coated dosage forms. Roland Bodmeier et al., Mechanical Properties of Drv and Wet Cellulosic and Acrylic Films Prepared from Aqueous Colloidal Polymer Dispersions used in the Coating of Solid Dosage Forms, Pharmaceutical Research, 11: 882-888 (1994).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, Super Saturation Mechanism of Drugs from Solid Dispersions with Enteric Coating Agents, Chem. Pharm. Bull. 36: 49414950 (1998). The solid dispersions are also referred to as solid-state dispersions. The term "coprecipitates" may also be used to refer to those preparations obtained by the solvent methods.

Solid dispersions may be used to improve the solubilities and/or dissolution rates of poorly water-soluble active agents. Hiroshi Yuasa, et al., Application of the Solid Dispersion Method to the Controlled Release Medicine. III. Control of the Release Rate of Slightly Water-Soluble Medicine From Solid Dispersion Granules, Chem. Pharm. Bull. 41:397-399 (1993). The solid dispersion method was originally used to enhance the dissolution rate of slightly water-soluble medicines by dispersing the medicines into water-soluble carriers such as polyethylene glycol or polyvinylpyraolidone, Hiroshi Yuasa, et al., Application of the Solid Dispersion Method to the Controlled Release of Medicine. IV. Precise Control of the Release Rate of a Water-Soluble Medicine by Using the Solid Disipersion Method Applying the Difference in the Molecular Weight of a Polymer, Chem. Pharm. Bull. 41:933-936 (1993).

The selection of the carrier may have an influence on the dissolution characteristics of the dispersed drug because the dissolution rate of a component from a surface may be affected by other components in a multiple component mixture. For example, a water-soluble carrier may result in a fast release of the drug from the matrix, or a poorly soluble or insoluble carrier may lead to a slower release of the drug from the matrix. The solubility of the active agents may also be increased owing to some interaction with the carriers.

Examples of carriers useful in solid dispersions according to the invention include, but are not limited to, water-soluble polymers such as polyethylene glycol, polyvinylpyraolidone, or hydroxypropylmethyl-cellul-ose. Akihiko Hasegawa, Application of Solid Dispersions of Nifedipine with Enteric Coating Agent to Prepare a Sustained-release Dosage Form, Chem. Pharm. Bull. 33: 1615-1619 (1985).

Alternate carriers include phosphatidylcholine. Makiko Fujii, et al., The Properties of Solid Dispersions of Indomethacin, Ketoprofen and Flurbiprofen in Phosphatidylcholine, Chem. Pharm. Bull. 36:2186-2192 (1988). Phosphatidylcholine is an amphoteric but water-insoluble lipid, which may improve the solubility of otherwise insoluble active agent in an amorphous state in phosphatidylcholine solid dispersions. See Makiko Fujii, et al., Dissolution of Bioavailibility of Phenyloin in Solid Dispersion with Phosphatidylcholine, Chem. Pharm. Bull 36:49084913 (1988).

Other carriers include polyoxyethylene hydrogenated castor oil. Katsuhiko Yano, et al., In-Vitro Stability and In-Vivo Absorption Studies of Colloidal Particles Formed From a Solid Dispersion System, Chem. Pharm. Bull 44:2309-2313 (1996). Poorly water-soluble active agents maybe included in a solid dispersion system with an enteric polymer such as hydroxypropylmethylcellulose phthalate and carboxymethylethylcellulose, and a non-enteric polymer, hydroxypropylmethylcellulose. See Toshiya Kai, et al., Oral Absorption Improvement of Poorly Soluble Drug Using Soluble Dispersion Technique, Chem. Pharm. Bull. 44:568-571 (1996). Another solid dispersion dosage form include incorporation of the drug of interest with ethyl cellulose and stearic acid in different ratios. Kousuke Nakano, et al., Oral Sustained-Release Cisplatin Preparations for Rats and Mice, J. Pharm. Pharmacol. 49:485-490 (1997).

There are various methods commonly known for preparing solid dispersions. These include, but are not limited to the melting method, the solvent method and the melting-solvent method.

In the melting method, the physical mixture of a drug in a water-soluble carrier is heated directly until it melts. The melted mixture is then cooled and solidified rapidly while rigorously stirred. The final solid mass is crushed, pulverized and sieved. Using this method a super saturation of a solute or drug in a system can often be obtained by quenching the melt rapidly from a high temperature. Under such conditions, the solute molecule may be arrested in solvent matrix by the instantaneous solidification process. A disadvantage is that many substances, either drugs or carriers, may decompose or evaporate during the fusion process at high temperatures. However, this evaporation problem may be avoided if the physical mixture is heated in a sealed container. Melting under a vacuum or blanket of an inert gas such as nitrogen may be employed to prevent oxidation of the drug or carrier.

The solvent method has been used in the preparation of solid solutions or mixed crystals of organic or inorganic compounds. Solvent method dispersions may prepared by dissolving a physical mixture of two solid components in a common solvent, followed by evaporation of the solvent. The main advantage of the solvent method is that thermal decomposition of drugs or carriers may be prevented because of the low temperature required for the evaporation of organic solvents. However, some disadvantages associated with this method are the higher cost of preparation, the difficulty in completely removing liquid solvent, the possible adverse effect of its supposedly negligible amount of the solvent on the chemical stability of the drug.

Another method of producing solid dispersions is the melting-solvent method. It is possible to prepare solid dispersions by first dissolving a drug in a suitable liquid solvent and then incorporating the solution directly into a melt of polyethylene glycol, obtainable below 70 degrees, without removing the liquid solvent. The selected solvent or dissolved active agent may be selected such that the solution is not miscible with the melt of polyethylene glycol. The polymorphic form of the active agent may then be precipitated in the melt. Such a unique method possesses the advantages of both the melting and solvent methods. Win Loung Chiou, et al., Pharmaceutical Applications of Solid Dispersion Systems, J. Pharm. Sci. 60:1281-1301 (1971).

Another controlled release dosage form is a complex between an ion exchange resin and the active agent. Ion exchange resin-drug complexes have been used to formulate sustained-release products of acidic and basic drugs. In one preferable embodiment, a polymeric film coating is provided to the ion exchange resin-drug complex particles, making drug release from these particles diffusion controlled. See Y. Raghunathan et al., Sustained-released drug delivery system I: Coded ion-exchange resin systems for phenylpropanolamine and other drugs, J. Pharm. Sciences 70: 379-384 (1981).

Injectable micro spheres are another controlled release dosage form. Injectable micro spheres may be prepared by non-aqueous phase separation techniques, and spray-drying techniques. Micro spheres may be prepared using polylactic acid or copoly(lactic/glycolic acid). Shigeyuki Takada, Utilization of an Amorphous Form of a Water-Soluble GPIIb/IIIa Antagonist for Controlled Release From Biodegradable Micro spheres, Pharm. Res. 14:1146-1150 (1997), and ethyl cellulose, Yoshiyuki Koida, Studies on Dissolution Mechanism of Drugs from. Ethyl Cellulose Microcapsules, Chem. Pharm. Bull. 35:1538-1545 (1987).

Other controlled release technologies that may be used in the practice of this invention are quite varied. They include SODAS, INDAS, IPDAS, MODAS, EFVAS, DUREDAS. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release minitablets. DUREDAS is a bilayer tablet formulation providing dual release rates within the one dosage form. Although these dosage forms are known to one of skill, certain of these dosage forms will now be discussed in more detail.

The active agent of the invention can be incorporated into any one of the aforementioned controlled released dosage forms, or other conventional dosage forms. The amount of active agent contained in each dose can be adjusted to meet the needs of the individual patient and the indication. One of skill in the art reading this disclosure will readily recognize how to adjust the level of active agent and the release rates in a controlled release formulation, in order to optimize delivery of active agent and its bioavailability.

Where the methods include delivery of a pharmaceutical agent, in certain embodiments the delivery devices and protocols described in U.S. Pat. No. 6,547,803; as well as United States Published Patent Applications Nos. 20040213770; 20040186435; 20040162542; 20040138643; 20040010309; 20030236494; 20030199852; 20030171734; and 20020198512. When such devices and protocols are employed in the methods of the present invention, the devices and protocols are employed such that adventitial biology is selectively modulated to achieve the desired outcome, consistent with the teachings above. As such, the devices and protocols are not employed to merely deliver agents to adventitial tissues such that the adventitial tissue serves as a depot for the delivered agents (whose action is ultimately directed to affecting other tissues), but instead are delivered to the adventitial tissue in order to directly modulate the biology thereof, and thereby achieve the desired therapeutic outcome. Furthermore, care is taken in certain of these embodiments to deliver the agent solely to the adventitia, and not to vascular tissue below the adventitial or to the perivascular regions beyond the adventitia itself. As such, in certain of these embodiments, agent is delivered solely to the adventitia, and an amounts and a manner effective to modulate biology solely of the adventitia and thereby achieve the desired therapeutic outcome. In certain embodiments, the agents selected, as well as mode of administration thereof, are done in a manner that modulates the sympathetic/parasympathetic bias of the adventitial tissue in a manner that achieves the desired therapeutic outcome.

Applying Electrical Energy

As noted above, certain embodiments include employing electrical modulation, in a manner effective to cause the desired selective adventitial modulation according to the subject methods.

Any suitable area may be targeted for electrical modulation. Areas that may be targeted include, but are not limited to, pre- and post ganglionic nerve fibers, as well as ganglionic structures, efferent and afferent nerve fibers, synapses, etc., and combinations thereof in certain embodiments. In certain embodiments, activity in a given nerve fiber may be electrically modulated in more than one area of the nerve fiber. In certain embodiments, electrical energy is applied to modulate synaptic efficiency, e.g., to increase or decrease the sensitivity of a synapse and include modulating presynpatic neurons.

As such, areas which may be targeted with electrical energy include, but are not limited to, pre- and post ganglionic nerve fibers, ganglionic structures, efferent and afferent nerve fibers, the hypothalamus, receptors any receptor described herein, afferent autonomic nerves (sympathetic and parasympathetic). Embodiments include receptors of the hypothalamus, including hormonal receptors on the hypothalamus. In certain embodiments, a given nerve fiber or the like may be targeted for electrical modulation in more than one area of the nerve fiber. Targeted areas of the nervous system which may be targeted in accordance with the subject invention include, but are not limited to, vagus nerve, otic ganglion, and sphenopalatine ganglion, internal carotid nerve and plexus, middle and superior cervical sympathetic ganglion; vertebral ganglion; cervicothoracic ganglion; sympathetic trunk; cervical cardiac nerves; cardiac plexus; thoracic aortic plexus; celiac ganglion; celiac trunk and plexus; superior mesenteric ganglion, superior mesenteric artery and plexus; intermesenteric plexus; inferior mesenteric ganglion; inferior mesenteric artery and plexus; superior hypogastric plexus; hypogastric nerves; vesical plexus; thoracic cardiac nerves; sympathetic trunk; 6th thoracic sympathetic ganglion; gray and white rami communicantes; greater, lesser and least splanchnic nerves; aorticorenal ganglion; lumbar splanchnic nerves; gray rami communicantes and sacral splanchnic nerves; and the like, or a combination of two or more of the above.

A number of different devices may be employed in accordance with the subject invention. For example, device and systems for applying electrical energy to a subject and which may be adapted for use in the subject invention are described, e.g., in copending U.S. patent application Ser. Nos.: 10/661,368, 10/871,366 and elsewhere, the disclosures of the US patent applications are herein incorporated by reference. Such devices may be positioned directly on a targeted area, e.g., positioned below the skin of a subject directly on or adjacent a portion of the nervous system (e.g., one or more nerve fibers) such as an implantable device, or may be an external device (i.e., some or all of the device may be external to the subject). In accordance with the subject invention, one or more electrodes or electrical contacts may be positioned directly on or adjacent a targeted area, where the one or more electrodes may be surgically implanted, e.g., directly on or adjacent a targeted nerve fiber of a subject. In certain embodiments, an immunomodulator such as a steroid or the like, may be incorporated into a surface contacting area of a device, e.g., to minimize inflammation of the targeted site.

An electric energy applying device typically includes a stimulator such as an electrode, a controller or programmer and one or more connectors for connecting the stimulating device to the controller. In certain embodiments more than one electrode may be employed. In further describing representative electrodes, such are described in the singular, but it will be apparent that more than one electrode may be used, where such may be the same or may be different in one or more aspects. Accordingly, the description of an exemplary electrode suitable for use in the subject methods is applicable to other electrodes that may be employed. The electrode employed in the subject invention is controllable to provide output signals that may be varied in voltage, frequency, pulse width, current and intensity. The electrode may be one that provides both positive and negative current flow from the electrode and/or may be capable of stopping current flow from the electrode and/or changing the direction of current flow from the electrode. For example, embodiments include an electrode that is controllable in these respects, i.e., controllable in regards to producing positive and negative current flow from the electrode, stop current flow from the electrode, change direction of current flow from the electrode, and the like. In certain embodiments, the electrode has the capacity for variable output, linear output and short pulse width.

The energy source for the electrical output may be provided by a battery or generator such as a pulse generator that is operatively connected to the electrode. The energy source may be positioned in any suitable location such as adjacent to the electrode (e.g., implanted adjacent the electrode), or a remote site in or on the subject's body or away from the subject's body in a remote location and the electrode may then be connected to the remotely positioned energy source using wires, e.g., may be implanted at a site remote from the electrode or positioned outside the subject's body in certain instances. Of interest are implantable generators analogous to a cardiac pacemaker. In addition, of interest are implantable devices capable of generating power from the endogenous thermodynamic and electric energy of the body.

The electrode may be mono-polar, bipolar or multi-polar. In order to minimize the risk of an immune response triggered by the subject against the device and minimize damage such as corrosion and the like to the device from other biological fluids, etc., the electrode and any wires and optional housing materials are made of inert materials such as for example silicon, metal, plastic and the like. For example, a multi-polar electrode having about four exposed contacts (e.g., cylindrical contacts) may be employed.

A controller or programmer may also be coupled with an electric energy applying device. The programmer is typically one or more microprocessors under the control of a suitable software program. Other components of the programmer will be apparent to those of skill in the art, e.g., analog to digital converter, etc. The electric energy applying device may be pre-programmed for desired parameters. In certain embodiments the parameters are controllable such that the electrode signal may be remotely modulated to desired settings without removal of the electrode from its targeted position. Remote control may be performed, e.g., using conventional telemetry with an implanted electric signal generator and battery, an implanted radiofrequency receiver coupled to an external transmitter, and the like. In certain embodiments, some or all parameters of the electrode may be controllable by the subject, e.g., without supervision by a physician. For example, a magnetic signal may be employed. In such embodiments, one or more magnets may be employed such that upon bringing a magnet in proximity to or away from the power source such as a pulse generator, the magnet may be employed to interfere with the electronic circuitry thus modulating the power—either increasing or decreasing the power supplied depending on whether the magnet is brought in proximity or moved away from the power source.

FIG. 1 shows an exemplary embodiment of an electric energy applying device 100. Device 100 may be implanted in a suitable position of a subject's body 10. One or more leads 23 are shown positioned to stimulatory or inhibitory electrical energy. Device 100 include energy source 14 which may take the form of a modified signal generator Model 7424 manufactured by Medtronic, Inc. under the trademark Intrel II. Lead 23 may take the form of any suitable lead, such as any of the leads that are sold with the Model 7427 and is coupled to energy source 14 by one or more conventional conductors 16 and 18. Lead 23 may include a paddle lead, a lead having one or more electrodes and/or catheters, or a combination catheter/lead capable of providing electrical impulses and pharmacological delivery. In certain embodiments, a lead may be composed of concentric tubes such as made of platinum or other like material. The tubes may be coated with a polymer except for the distal portions that may serve as the electrodes. Conductive wires carrying energy to the electrodes may be in the interior of the concentric tubes. Optionally, a distal electrode end may include a small recording microelectrode to help assist in the actual placement of the lead.

The present invention may be operated as an open-loop controlled system. In an open-loop system, the physician or patient may at any time manually or by the use of pumps or motorized elements adjust treatment parameters such as pulse amplitude, pulse width, pulse frequency, or duty cycle. Optionally, the present invention may incorporate a closed-loop control system which may automatically adjust the electrical parameters in response to a sensed parameter or condition of a subject. Under a closed-loop feedback system to provide automatic adjustment of parameters of the electrodes, a sensor that senses a condition of the body is utilized. More detailed descriptions of sensors that may be employed in the practice of the subject invention, and other examples of sensors and feedback control techniques that may be employed are disclosed in U.S. Pat. No. 5,716,377, which is incorporated herein by reference.

As shown in FIG. 1, the distal end of lead 23 terminates in one or more delivery elements such as stimulation electrodes which may be implanted using conventional surgical techniques. The type of treatment that is desired determines the location of the electrodes. Any number of electrodes may be used for various applications. Each of the electrodes may be individually connected to energy source 14 through lead 23 and conductors 16 and 18. Lead 23 may be surgically implanted either by a laminotomy or by a needle.

Energy source or signal generator 14 may be programmed to provide a predetermined stimulation (or inhibition) dosage in terms of pulse amplitude, pulse width, pulse frequency, or duty cycle. As shown, a programmer 20 may be utilized to provide stimulation (or inhibition) parameters to the delivery device via any suitable technology, e.g., using telemetry and the like. For example, in using telemetry, programmer 20 may be coupled to an antenna 24 via conductor 22. In certain embodiments, the programmer may be positioned, e.g., implanted, inside body 10. For example, in certain embodiments the programmer may be integrated with the energy source, electrode, etc., for example as a single unit.

Device 100 may optionally include one or more sensors to provide closed-loop feedback control of the treatment and/or electrode positioning. One or more sensors (not shown) may be attached to or implanted into a portion of a subject's body suitable for detecting a physical and/or chemical indicator of the subject. For example, sensing feedback may be accomplished, e.g., by a mechanical measure within a lead or an ultrasound or other sensor to provide information about the treatment parameters, lead positioning, LTP, etc.

Operative placement of a suitable electric energy applying device may be accomplished using any suitable technique. An electrode introducer needle may be employed to implant the electrode on or proximate to the area of interest. The size of the introducer needle may vary depending on the diameter of the electrode, etc., where in certain embodiments the electrode introducer needle may be a 12-gauge, 14-gauge, 16-gauge, 18-gauge, 20-gauge needle or 22-gauge needle, e.g., an electrode introducer needle available from Radionics in the Sluyter-Mehta kit as SMK 100 mm 2 mm active tip cannula. However, it should be understood that other electrode introducer needles may be used as appropriate to the needs and skill level of the practitioner performing the surgical procedure.

At least one imaging apparatus such as a CT scan, MRI apparatus, ultrasound apparatus, fluoroscope, or the like, may be employed to monitor the surgical. For exemplary purposes only, the subject method will be described using a fluoroscope, where such is in no way intended to limit the scope of the invention. The subject is placed in a suitable position for access e.g., supine, on a fluoroscopy table, with the patient's nose pointing vertically. The fluoroscope is then adjusted to a straight lateral position. And the entry point for the insertion of the electrode is determined.

Once the entry point is determined, the skin overlying the entry point is shaved and prepared with antiseptic solution. A 25-gauge needle may be used to inject a subcutaneous local anesthetic (such as, for example, 2 cc of 2% lidocaine) into the skin and subcutaneous tissues overlying the entry point. In addition to the local anesthetic, the patient may be given intravenous sedation and prophylactic antibiotics prior to commencement of the implantation procedure if desired. The electrode introducer needle is inserted at the entry point and advanced. The fluoroscope may be adjusted as the needle is advanced. Once the needle is positioned the stylet is withdrawn from the electrode introducer needle. Once the implanted electrode is in place, the end of the electrode that is outside the skin is carefully held in place against the skin. The electrode introducer needle may then be slowly removed, leaving the implanted electrode in place. At this point, if desired, a few small subcutaneous sutures may be placed around the electrode to hold it in the desired position.

Once the needle has been completely removed and the implanted electrode is in the final position, then the proximal part of the electrode that is coming out of the skin may be secured to the skin of the subject, e.g., by adhesive tape. Additionally, a small incision may be made on the skin at the area the electrode exits the face. Then several subcutaneous sutures may be placed around the electrode to hold it in place. The distal end of the electrode may then be connected to an extension wire or catheter, which is tunneled to the subclavicular area, or another region which will house the device used as an energy source for the implanted electrode. The device or devices used to control the electrode may be surgically implanted in the desired region by procedures known in the art, such as have been applied in surgical neuromodulation therapies used to treat Parkinson's disease. In certain embodiments of the subject invention, an electrode may be utilized which, instead of or in addition to delivering electric impulses to at least a portion of the autonomic nervous system, delivers a pharmacological agent to at least a portion of the autonomic nervous system. For example, an electrode may be used that has a small port at its tip which is connected to a reservoir or pump containing a pharmacological agent. The pharmacological agent delivery electrode may be implanted using an analogous procedure as that described above for the autonomic system modulating-electrode. In certain embodiments the reservoir or pump may also be implanted in the subject's body, analogous to that described above for the electrical impulse generator. The pharmacological agent delivery electrode may be controllable such that the amount of pharmacological agent delivered, the rate at which the pharmacological agent may be delivered, and the time period over which the pharmacological agent is delivered may be adjusted.

In embodiments in which electrical energy is used, any suitable protocol may be used, where certain protocols include using an electric energy applying device to deliver a suitable amount of electrical energy to a subject. Once an electric energy applying device is positioned in a suitable position on or about one or more targeted areas electrical energy is applied thereto for a period of time sufficient to provide the desired effect. This period of time will vary depending on the area (e.g., the nerve fiber) being treated, the condition being treated, etc. Certain embodiments include simultaneously monitoring (i.e., in "real time") the as aspect of the nervous system such that a given nerve fiber may be electrically stimulated (or electrically inhibited) until the desired result is observed. Still further, in many embodiments once the desired result is achieved, a targeted area may be repeatedly electrically stimulated (or inhibited) one or more times to maintain the desired state such that the subject methods may be repeated one or more times, i.e., the subject methods include chronically applying electrical energy to a subject, such as chronically applying electrical energy to one or more nerve fibers. For example, in certain embodiments electrical stimulation (e.g., intermittent mild electrical pulses) may be delivered to a given area of the nervous system, twenty-four hours a day for a period of days, weeks, months, or even years in certain embodiments.

During the period of time that electrical energy is applied to a given area, the electrical energy may be substantially continuous, including continuous or intermittent (i.e., pulsed or periodic), where in many embodiments the electrical energy is in the form of electrical pulses. In other words, in certain embodiments electrical energy may be given continuously during the above-described period of time and in certain embodiments electrical energy may be given to an area in a pulsed or intermittent manner during the period of time described above. In accordance with the subject methods to apply electrical energy to a subject, once operatively positioned the electric energy applying device is activated to provide an electrical signal to the targeted area in a manner effective to practice the subject methods.

In practicing the subject methods, activation of the electric energy applying device directly applies the electrical output of the device, i.e., electrical impulses, to the targeted area. The exact parameters of the applied electrical energy may vary depending on the particular subject, condition being treated, etc. For example, an electronic current wave may be provided when the electrical energy is applied. In certain embodiments, the current wave includes current waves of high frequency, e.g., high frequency pulses, where the current wave may also include low frequency amplitude modulation. In certain embodiments, a plurality of high frequency bursts of current pulses may be applied in addition to the application of underlying low frequency continuous stimulus. Stimulation may be monopolar or multipolar. For example, to stimulate a targeted area, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 1 Hz to about 1000 Hz, e.g., from about 2 Hz to about 100 Hz in certain embodiments. In certain embodiments a pure d-c voltages may be employed. The pulse width may range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds. The electrical output may be applied for at least about 1 millisecond or more, e.g., about 1 second, e.g., about several seconds, where in certain embodiments the stimulation may be applied for as long as about 1 minute or more, e.g., about several minutes or more, e.g., about 30 minutes or more may be used in certain embodiments.

In certain embodiments, a control feedback loop is provided. For example, during or following a particular electric energy applying protocol, a biological aspect of a subject may be monitored, e.g., by sensing conduction in a neuronal system, e.g., in a particular electrically stimulated nerve fiber, or by any suitable method. For example, a sensor suitable for detecting nerve cell or axon activity may be implanted in a portion of a subject's body. A sensor may take the form of an electrode or the like. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. In utilizing a feedback system, if predetermined detection criteria are not detected, the same or a different stimulus protocol may be performed and may be automatically initiated under the control of a controller. For example, in those instances where a different protocol is performed, one or more of the electrical energy applying parameters may be modified, e.g., the pulse width may be increased, or the like, in the second protocol.

In addition to electrical energy applying devices, devices to withdraw electrical energy from the site of treatment, to create electrical current flow within the site of treatment, to create differential alignment of charge within the site of treatment, to alter the conductance/resistance characteristics of the site of treatment, as well as to impose magnetic fields upon or derive magnetic fields from the site of treatment, also are candidates for mechanisms by which to impose therapeutic interventions. As such, of interest are devices that electrically modulate the site of treatement, e.g., the adventitia.

Certain embodiments may entail endovascular delivery of the stimulus producing device. Other embodiments may involve laparoscopic delivery of the device; others may require surgical placement; and still others may require transcutaneous delivery of the appropriate stimulus.

Utility

The subject methods find use in a variety of applications, as reviewed above. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. In certain embodiments, such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Computer Readable Mediums and Programming Stored Thereon

The subject invention includes computer readable media having programming stored thereon for implementing the subject methods. For example, the subject invention may include suitable computing means such as suitable hardware/software for performing the subject methods.

In certain embodiments, programming may control a device to administer a pharmacological agent to a subject, e.g., programming may be configured to determine suitable dosage, etc. In certain embodiments programming may control a device to administer electrical energy to a subject, e.g., may control the activation/termination of electrical energy including selecting suitable electrical parameters. Programming may be configured to, or otherwise be capable of, directing a microprocessor to activate, i.e., turn "on" and "off" an electric energy applying device for applying energy to a subject. For example, if so determined, the processor may direct the electric energy applying device to provide the appropriate energy to result in the desired action. Accordingly, a processor may select the appropriate parameters (e.g., frequency, amplitude, etc.) depending on what is required and direct an electric energy applying device to implement the parameters. Programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out the subject methods, where such an algorithm is used to direct a processor or series of processors to execute the steps necessary to perform the task(s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means and process that information to determine if intervention is required. The result of that processing may be communicated to a user, e.g., via audio and/or visual means, e.g., the algorithm may also include steps or functions for generating a variety of profile graphs, plots, etc.

The subject invention may also include a data set of known or reference information stored on a computer readable medium to which data collected may be compared for use in determining a given treatment regimen. The data may be stored or configured in a variety of arrangements known to those of skill in the art.

Kits

Also provided are kits for practicing the subject methods. Kits may include an electric energy applying device, as described above. Devices for delivering, e.g., implanting, an electric energy applying device to a target site of a subject such as into the body cavity of a subject may also be included in the subject kits. For example, an endoscope, introducer needle, and the like may be provided. Of interest in certain embodiments are the delivery devices described in U.S. Pat. No. 6,547,803; as well as United States Published Patent Applications Nos. 20040213770; 20040186435; 20040162542; 20040138643; 20040010309; 20030236494; 20030199852; 20030171734; and 20020198512 (the disclosures of which are herein incorporated by reference) which can be employed as adventitial tissue specific delivery devices.

The subject kits may also include one or more pharmacological agents, as described above. The dosage amount of the one or more pharmacological agents provided in a kit may be sufficient for a single application or for multiple applications. Accordingly, in certain embodiments of the subject kits a single dosage amount of a pharmacological agent is present and in certain other embodiments multiple dosage amounts of a pharmacological agent may be present in a kit. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit is dictated by the particular pharmacological agent employed, as describe above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperiactivityal, intradermal, transdermal, intracheal, etc. Accordingly, certain systems may include a suppository applicator, syringe, I.V. bag and tubing, electrode, etc.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

EXPERIMENTAL

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Direct Administration of Anti-Inflammatory Agents to Carotid Artery Adventitia to Treat Atherosclerosis Double-blinded randomized controlled studies are employed to ascertain the effect of direct administration of anti-inflammatory agents to vessel wall adventitia in carotid atherosclerotic disease. Subjects are selected on the basis of extent of carotid occlusion as determined by ultrasound and MRI. Administration of the anti-inflammatory agent is performed in all subjects in the treatment group via surgical isolation of the carotid artery and affixation of a polymer patch containing the anti-inflammatory agent to the external aspect of the artery. Control subjects undergo the same procedure and receive a patch of similar structure but containing placebo. Administration of the anti-inflammatory agent produces statistically significant diminution of atherosclerotic occlusion over a six-month study period for the treatment group compared to control as determined by ultrasound and MRI.

As such, selective adventitial administration of an anti-inflammatory agent results is an effective treatment for diseases characterized by the presence of atherosclerotic occlusion.

Example 2: Remote Electrical Stimulation to Increase Sympathetic Activity Supplying the Uterine Artery Adventitia to Treat Fibroids The uterus represents a model paradigm for the role of vascular biology in overall organ function, as both the pathologic process of fibroid development and the felicitous maintenance of fertility appear to depend on judicious control of appropriate blood flow through relevant channels.

Double-blinded randomized controlled studies are employed to determine the effect of electrical stimulation of autonomic nerves supplying the adventitia of the uterine artery in reducing the size of uterine myomata. Subjects are selected on the basis of possession of fibroids within particular size and number constraints. Isolation and identification of relevant nerves is performed by placement of monitoring electrodes on the adventitia of the uterine artery and sequential stimulation of nearby nerves until an appropriate response is achieved. An electrical device for stimulation is adapted for application to relevant nerve bundles. The electrodes for this device consist of bipolar electrodes that generate action potentials by cathodic stimulation and produce a complete anodal block on one side of the cathode to make the electrode-generated action potentials unidirectional. Each bipolar electrode contains an insulating base with cathode and anode on one face and control circuitry on the opposite face. This apparatus communicates with a master control unit either attached to the bipolar electrodes directly via an asynchronous serial bus or via wireless communication link. 1-5 Hz has been described as the frequency that best describes the conduction velocity, latency, and refractory period of sympathetic nerves, and range of amplitude of current delivered can vary between 0.1 and 20 A. Subjects in the treatment group receive stimulation of the isolated relevant nerves using an implanted neurostimulation device. Control subjects have similar devices implanted but do not receive any pulsed stimulation for the duration of the treatment period. Electrical stimulation of sympathetic activity supplying the adventitia of the uterine artery is observed to cause a statistically significant decrease in fibroid size over a predetermined study period for the treatment group compared to control.

Example 3: Application of Organ Harness to Increase Sympathetic Activity Supplying the Adventitia of the Uterine Vasculature to Reduce Fibroids Double-blinded randomized controlled studies are employed to ascertain the effect of application of an organ harness to stimulate sympathetic activity in the adventitia of the overall uterine vasculature in reducing the size of uterine myomata. Subjects are selected on the basis of possession of fibroids within particular size and number constraints. Treatment subjects receive an organ harness deployed on the uterus via a minimally invasive approach. The organ harness consists of a hinged canopy of interlinked Nitinol members designed to ensheath the apex of the uterus. Application of electrical current to the canopy produces contraction via alteration of resistive force and creation of bending moments throughout the structure. This apparatus communicates with a master control unit to supply the current. Control subjects have devices of similar structure but of inert non-resistive material deployed for the duration of the treatment period. Application of the organ harness is observed to cause a statistically significant decrease in fibroid size over a predetermined study period for the treatment group compared to control.

Example 4: Transcervical Administration of Adrenergic Agents to Increase Sympathetic Activity Supplying the Adventitia of the Uterine Vasculature to Enhance Fertility Double-blinded randomized controlled studies are employed to ascertain the effect of administration of adrenergic agents administered via a transcervical approach to stimulate sympathetic activity in the adventitia of the adjacent uterine vasculature in enhancing fertility. Subjects are selected on the basis of lack of successful conceptions despite active ongoing attempts over a predetermined period. Treatment subjects receive a small molecule adrenergic agent in a topical formulation for direct application to the cervix at a prescribed frequency. Control subjects receive the formulation base as placebo for application at the same schedule of administration. Application of the transcervical adrenergic agent to is observed to promote sympathetic activity supplying the adventitia of the uterine vasculature to produce a statistically significant enhancement of fertility in the treatment group compared to control.

Example 5: Systemic Administration of Anti-Inflammatory Agents Targeted to the Adventitia to Treat Thromboangiitis Obliterans Double blinded randomized controlled studies are employed to ascertain the effect of systemic administration of anti-inflammatory agents linked to carrier molecules that caused specific targeting of the adventitia of vessels in treating thromboangiitis obliterans, a relatively adventitia-specific vasculitis. Subjects are selected on the basis of the presence of thromboangiitis obliterans proven by biopsy. Treatment subjects receive the targeted anti-inflammatory agent via infusion at a prescribed frequency. Control subjects receive the same agent, albeit without targeting, at the same schedule and via the same route. Systemic administration of anti-inflammatory agents targeted to the adventitia is observed to produce a statistically significant reduction in severity of thromboangiitis obliterans in the treatment group compared to control.

Example 6: Direct Administration of Botulinum Toxin to Blood Vessel Adventitia and Media to Treat Atherosclerosis Double-blinded randomized controlled studies are employed to ascertain the effect of direct administration of botulinum toxin to vessel wall adventitia and media in atherosclerotic disease. Subjects are selected on the basis of extent of vessel occlusion as determined by ultrasound and MRI. All subjects in the treatment group receive botulinum toxin via administration to the external aspect of the affected vessel wall. One mechanism to effect delivery employs transmural injection via needle extension from an intraluminal catheter. Control subjects undergo the same procedure, but receive placebo. Administration of the botulinum toxin is observed to produce a statistically significant diminution of atherosclerotic occlusion over a six-month study period for the treatment group as compared to the control group, as determined by ultrasound and MRI.

Example 7. Adventitial Dysfunction: A New Model for Understanding Atherosclerosis The inventors here for the first time appreciate the adventitia as a target for correcting and preventing atherosclerotic disease. The differential response of adventitia compared to intima with respect to known agents demonstrates the potential for rediscovery or redeployment of ignored or marginalized agents to achieve greater activity and selectivity. A variety of different approaches may be used to treat atherosclerosis via selective modulation of adventitial tissue, including mechanical and biopharmaceutical approaches, including administration of agents to the external rather than the internal aspect of vessels, utilization of polymers or coatings that enclose or encase vessels rather than line them, and deployment of agents with a greater emphasis on neuromodulation.

All publications and patents and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of treating a subject for atherosclerosis, said method consisting of:

modulating inflammatory activity of the adventitial tissue of a target artery of said subject by direct application of a pharmacological agent from an extravascular location to the surface of the adventitia at an affected portion of the target artery while avoiding a disturbance of extant derangement within the target artery, and in a manner effective to treat atherosclerosis.

2. The method according to claim 1, wherein said method comprises modulating the sympathetic/parasympathetic bias of said adventitial tissue of said subject.

3. The method of claim 1, wherein said method involves direct application of a stimulus to the adventitia of vessels adjoining a target region of a vessel.

4. The method of claim 1, wherein said method involves direct application of a stimulus to the autonomic nerves supplying the adventitia of the target vessel/s.

5. The method of claim 1, wherein said method involves direct application to the baroreceptors influencing the biology of the adventitia of the target vessel/s.

6. The method of claim 1, wherein said method involves direct application of a stimulus to the chemoreceptors influencing the biology of the adventitia of the target vessel/s.

7. The method of claim 1, wherein said method involves direct application of a stimulus to the volume receptors influencing the biology of the adventitia of the target vessel/s.

8. The method of claim 1, wherein said method involves direct application of a stimulus to adjacent readily accessible tissue structures physically linked to the adventitia of the target vessel/s.

9. The method according to claim 1, wherein said pharmacologic agent is delivered in a pulsatile fashion.

10. The method according to claim 9, wherein said pharmacologic agent is delivered according to a predetermined schedule.

11. The method according to claim 1, wherein said pharmacologic agent is delivered in response to the measurement of desired target parameters.

12. The method according to claim 1, wherein said pharmacologic agent is delivered via an external patch.

13. The method according to claim 1, wherein said modulating comprises administering a second pharmacologic agent.

14. The method according to claim 1, wherein said pharmacological agent is applied to the surface of the adventitia by a pharmacological agent delivery device applied to the external aspect of said target artery.

15. The method according to claim 1, wherein said pharmacological agent is an anti-inflammatory agent.

16. The method according to claim 14, wherein said pharmacological agent delivery device comprises an implantable patch configured to be affixed to an external aspect of the target artery.

17. The method according to claim 1, wherein said pharmacological agent is applied to the subject in a controlled release form.

18. The method according to claim 1, wherein the pharmacological agent is released via a rate-preprogrammed delivery system.

19. The method according to claim 1, wherein the application of the pharmacological agent is automatically released via a feedback-regulated delivery system.

20. The method according to claim 19, wherein automatic release of the pharmacological agent is triggered by the occurrence of a biochemical event in said subject.

* * * * *